United States Patent [19]

Pillot et al.

[11] Patent Number: 4,778,908

[45] Date of Patent: Oct. 18, 1988

[54] PROCESS FOR PREPARING DISILYLMETHANES

[75] Inventors: Jean-Paul Pillot, Cestas; Claude Biran; Eric Bacque, both of Talence; Paulette Lapouyade, Gradignan; Jacques Dunogués, Talence; Pierre Olry, Bordeaux, all of France

[73] Assignee: Societe Europenne de Propulsion, Suresnes, France

[21] Appl. No.: 55,692

[22] Filed: May 29, 1987

[30] Foreign Application Priority Data

May 30, 1986 [FR] France ................. 86 07814

[51] Int. Cl.$^4$ ............................................. C07F 7/08
[52] U.S. Cl. ................................................... 556/435
[58] Field of Search ......................................... 556/435

[56] References Cited

U.S. PATENT DOCUMENTS

| | | | |
|---|---|---|---|
| 2,507,518 | 5/1950 | Goodwin | 556/435 |
| 2,557,942 | 6/1951 | Clark | 556/435 |
| 3,308,146 | 3/1967 | Merker | 556/435 X |
| 4,414,403 | 11/1983 | Schilling et al. | 556/430 |

FOREIGN PATENT DOCUMENTS

| | | | |
|---|---|---|---|
| 1334850 | 7/1963 | France | 556/435 X |
| 2163792 | 7/1973 | France . | |
| 0733570 | 7/1955 | United Kingdom | 556/435 |
| 0740991 | 11/1955 | United Kingdom | 556/435 |

OTHER PUBLICATIONS

Noll, "Chemie und Technologie der Silicone", pp. 43–44, Verlag Chemie GmbH, 1968.
"Inorganic Chemistry", 4, pp. 149–150, Buttersworth (London).
"Chem. Abs.", 58, 9114h (1963).
"Chem. Abs.", 58, 9115a (1963).
"J. Chem. Soc.", 1971, pp. 3617–3620.
"J. of Gen. Chem. of the USSR", 97, 1608–1609, 1977.
"J.A.C.S.", 85, p. 2243–2244, 1963.

*Primary Examiner*—Paul F. Shaver
*Attorney, Agent, or Firm*—Willian Brinks Olds Hofer Gilson & Lione Ltd.

[57] ABSTRACT

The present invention relates to a process for preparing disilylmethanes, wherein the magnesian reaction is carried out between methylene chloride and at least one chlorosilane in a donor solvent.

6 Claims, No Drawings

PROCESS FOR PREPARING DISILYLMETHANES

The present invention relates to a process for preparing disilylmethanes.

Disilylmethanes are compounds of formula:

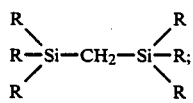

such products, and more particularly the dichloro derivatives in -1,3 position, may constitute potentially very interesting intermediates. Unfortunately, no simple and general process for preparing these disilylmethanes is known.

It is an object of the present invention to present a simple and inexpensive process for preparing the disilylmethanes defined hereinafter.

This process is characterized in that the reaction of methylene chloride ($CH_2Cl_2$) is carried out with a chlorosilane

this reaction being a magnesian reaction, i.e. involving the presence of magnesium and of an anhydrous solvent of the donor type.

In addition, it has been found that the reaction could be facilitated by the presence of another metal of which it is thought that it presents the possibility of activating either the methylene chloride or the magnesium, this metal being zinc, cadmium, copper, aluminium or mercury, but preferably zinc. The quantities of the metal that may be used are generally included between 5% and 70% by weight of the magnesium used, a quantity of metal less than 5% having little effect on the reaction, and a quantity of metal greater than 70% being useless and sometimes detrimental as it is capable of inducing secondary reactions.

The reaction between methylene chloride and chlorosilane may be written as follows:

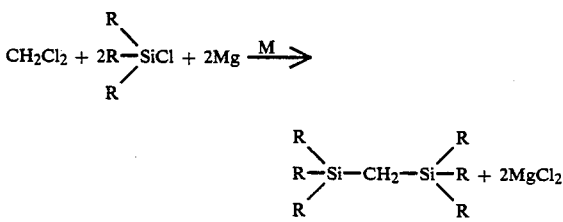

The three radicals R of the chlorosilane may be identical or different and may be selected from H, alkyl, cycloalkyl, aryl, arylalkyl, alkylaryl, alkenyl, possibly substituted, and Cl.

The chlorosilanes that may be used as reagents are either pure products or mixtures, for example, the residues of the direct industrial synthesis of methylchlorosilanes.

The solvents of the donor type which may be used are those known for the magnesian synthesis, for example ether, DME (dimethoxyethane) or THF (tetrahydrofuran) and N-2-methylpyrrolidone. Among these solvents, the preferred one is THF.

The reaction takes place at a temperature of between about 10° and 70° C.; this temperature depends in particular on the properties of the solvent and on the reagents used. It is preferably carried out in an inert atmosphere.

The reaction according to the invention is relatively slow, requiring a duration of between about 8 and 72 hours.

At the end of the reaction, a liquid (solvent) is obtained in which are dissolved the final product, possibly certain soluble complexes of the Mg and of the metal, and solids which are constituted by derivatives of the magnesium and of the metal. The liquid is separated from the solid either by filtration or by distillation of the liquid; in the resulting liquid, the final product is generally obtained by fractional distillation.

The following non-limiting Examples illustrate the invention.

EXAMPLE 1

Preparation of $[(CH_3)_2H\ Si]_2CH_2$

A dried reactor equipped with a dropping funnel, a magnetic stirrer, a bulb cooler and an inlet of inert gas (argon) is used.

0.4 mol (37.8 g) of $(CH_3)_2HSiCl$, 0.1 mol of $CH_2Cl_2$ (8 5 g), 0.2 gram-atom (4.86 g) of Mg and 3 g of zinc are introduced into this reactor.

200 ml of tetrahydrofuran (THF) are then introduced dropwise into the reactor.

The temperature is maintained at 40° C.

After 24 hrs. heating, the reaction is stopped; after cooling, the volatile products are evaporated in vacuo by a vane pump and collected in a trap *cooled by liquid nitrogen.*

After heating, the product collected in the trap is distilled in a winding band column and the following is collected:

at the head (maximum temperature 70° C.), the solvent;
in the intermediate part (70° to 105° C.) a little final product, but also containing a little solvent;
at 105° C., the pure product which represents about 9.4 g; yield: 71%.

N.B. In this Example and in the following Examples, the yields are calculated with respect to the methylene chloride employed.

EXAMPLE 2

An apparatus similar to that described in Example 1 is used.

170 g of $CH_2Cl_2$, 1150 g of $CH_3SiHCl_2$, 97.3 g of magnesium turnings and 40 g of zinc powder are introduced into the reactor.

Some drops of tetrahydrofuran (THF) are added, this triggering off the reaction and the temperature rises. This temperature is returned to about 20° C. and tetrahydrofuran is progressively added for 10 hours. The total quantity of tetrahydrofuran introduced has thus attained 1500 ml.

The reaction is allowed to continue so that the total duration is about 48 hours.

Separation is effected:

on the one hand, by evaporating the volatile products with the aid of a filter pump protected by a trap cooled by a dry-ice/acetone mixture in order to recover the excess chlorisilane and the THF, on the other hand, by washing the pasty solid which remains in the reactor after the evaporation described hereinabove, with 3 times 700 ml of hexane and by filtering the medium obtained in an inert atmosphere.

The organic phases obtained in these two operations are united, and the heads (up to 110° C.) constituted essentially by solvent, on the one hand, and, on the other hand, a heart and a residue which contain the desired disilylmethane, are recovered by distillation. The heart comprises about 104 g of $(CH_3SiHCl)_2CH_2$ (yield: 30%); the residues contain a proportion of this same disilylmethane which is appreciable but which has not been determined.

EXAMPLE 3

Preparation of $(PhMe_2Si)_2CH_2$

An apparatus similar to that described in Example 1 is used. 8.5 g of $CH_2Cl_2$, 40 g of $PhMe_2SiCl$, 4.9 g of Mg turnings and 13 g of Zn powder are introduced into the reactor. A few drops of tetrahydrofuran are added, which triggers off the reaction, and the temperature rises. THF is progressively added (100 ml) for 3 hrs. and the temperature of the medium is maintained at 40° C. The reaction is allowed to continue so that the total duration is about 90 hrs. A treatment similar to that of Example 2 then leads to the expected disilylmethane with a yield of 35.2% after distillation (b.p.$_{0.5}$=115° C., 10.0 g).

EXAMPLE 4

Preparation of $(CH_2=CHSiMe_2)_2CH_2$

An apparatus similar to that described in Example 1 is used. 8.5 g of $CH_2Cl_2$, 30 g of $CH_2=CHSiMe_2Cl$, 4.9 g of Mg turnings and 5.2 g of Zn powder are introduced into the reactor. Some drops of tetrahydrofuran are added, which triggers off the reaction, and the temperature rises. A (60/40 mL) solvent THF/diethylether mixture is progressively added for three hours, and the temperature of the medium is maintained at 25° C. It is then heated to 40° C. (total duration: 48 hrs.). A treatment similar to that of Example 1 leads to the desired disilylmethane with a yield of 28% after distillation (b.p.$_{30}$=75° C., 5.2 g).

EXAMPLE 5

Preparation of $(EtSiH_2)_2CH_2$

An apparatus similar to that described in Example 1 is used. 8.5 g of $CH_2Cl_2$, 19 g of $EtSiH_2Cl$, 4.9 g of Mg and 5.2 g of Zn powder are introduced into the reactor. Some drops of THF are added, which triggers off the reaction, and the temperature rises. THF is progressively added (total quantity: 180 mL in 4 hours), the temperature of the medium being controlled at 30° C. The medium is then left at ambient temperature (20° C.) for 48 hours. A treatment similar to that of Example1 leads to the desired disilylmethane with a yield of 38.7% after distillation (b.p.$_{760}$=128° C., 5.1 g).

EXAMPLE 6

Preparation of $(PhHSiCl)_2CH_2$

An apparatus similar to that of Example 1 is used. 4.3 g of $CH_2Cl_2$, 35 g of $PhSiHCl_2$, 2.5 g of Mg turnings and 2.6 g of Zn powder are introduced into the reactor. Some drops of THF are added, which triggers off the reaction, and the temperature rises. THF (50 ml) is progressively added for 2 hours, the temperature of the reaction medium being controlled at 30° C. The medium is allowed to react at ambient temperature for 48 hrs. A treatment similar to that of Example 2 leads to the desired disilylmethane with a yield of 71% (b.p.$_{35}$: 81° C., 10.5 g).

EXAMPLE 7

Preparation of $[(CH_3)_3Si]_2CH_2$

An apparatus similar to that described in Example 1 is used. 8.5 g of $CH_2Cl_2$, 25 g of $Me_3SiCl$, 4.9 g of Mg turnings and 5.2 g of zinc powder are introduced into the reactor. Some drops of tetrahydrofuran are added, which triggers off the reaction, and the temperature rises. The solvent is progressively added for 3 hrs., the temperature of the medium being maintained at 40° (total quantity of THF introduced: 100 mL). Total duration of the reaction: 48 hrs. A treatment similar to that of Example 1 leads to the expected bis(trimethylsilyl)methane with a yield of 45% after distillation (7.2 g, b.p.$_{760}$=125° C.)

EXAMPLE 8

A test similar to those described in the preceding Examples was repeated, from a mixture of chlorosilanes, residues of the direct industrial synthesis of methylchlorosilanes, having for approximate formula: $Me_{2.3}Cl_{3.7}Si_2$. The quantities of reagents were as follows: chloro disilanes: 44.3 g; $CH_2Cl_2$: 31.25 g; Mg: 17.9 g; Zn: 5 g; THF (solvent): 250 mL. After having taken the reaction mixture to a temperature of 50°-60° C. for 60 hours, a yellow oil (27.13 g) was obtained, of which analysis showed that it was essentially constituted by bi- or tridimensional disilylmethylene oligomeric chain formations.

We claim:

1. A process for preparing disilylmethanes comprising reacting methylene chloride with at least one chlorosilane, in an electron donor solvent, in the presence of magnesium and zinc, the amount zinc used being from about 5% to about 70% (weight:weight) of the amount of magnesium used.

2. The process according to claim 1, characterized in that the chlorosilane has for its formula:

in which the radicals R, which may be identical or different, are selected from the group consisting of H, alkyl, cycloalkyl, alkenyl, aryl, arylalkyl, alkylaryl radicals, possibly substituted, and Cl.

3. The process according to claim 1, characterized in that the chlorosilane is a residue of the direct industrial synthesis of the chlorosilanes with fraction boiling between 130° and 150° C. under atmospheric pressure.

4. The process according to any one of claims 1 to 3, characterized in that the electron donor solvent is selected from the group consisting of ether, dimethoxyethane, tetrahydrofuran and N-2-methylpyrrolidone.

5. The process according to claim 4, characterized in that the reaction is carried out at a temperature from about 10° to about 70° C. for a time of from about 8 to about 72 hours.

6. The process according to any one of claims 1 to 3, characterized in that the reaction is carried out at a temperature of from about 10° to about 70° C. for a duration of from about 8 to about 72 hrs.

* * * * *

UNITED STATES PATENT AND TRADEMARK OFFICE
CERTIFICATE OF CORRECTION

PATENT NO. : 4,778,908
DATED : October 18, 1988
INVENTOR(S) : Jean-Paul Pillot et al.   Page 1 of 2

It is certified that error appears in the above-identified patent and that said Letters Patent is hereby corrected as shown below:

On the cover sheet, after the heading "Assignee", please delete "Europenne" and substitute therefor --Europeenne--.

IN EXAMPLE 1

In column 2, lines 28 and 29, please delete "(8 5 g)" and substitute therefor --(8.5 g)--.

In column 2, line 40, before "at" please insert -- - --.

In column 2, line 41, before "in" please insert -- - --.

In column 2, line 43, before "at" please insert -- - --.

IN EXAMPLE 2

In column 2, line 65, before "on" please insert -- - --.

UNITED STATES PATENT AND TRADEMARK OFFICE
CERTIFICATE OF CORRECTION

PATENT NO. : 4,778,908

DATED : October 18, 1988

INVENTOR(S) : Jean-Paul Pillot et al.

Page 2 of 2

It is certified that error appears in the above-identified patent and that said Letters Patent is hereby corrected as shown below:

In column 3, line 1, before "on" please insert -- - --.

IN EXAMPLE 5

In column 3, line 55, please delete "Example1-" and substitute therefor --Example 1--.

Signed and Sealed this

Twelfth Day of February, 1991

Attest:

HARRY F. MANBECK. JR.

*Attesting Officer*         *Commissioner of Patents and Trademarks*